US012246084B2

(12) United States Patent
Liu et al.

(10) Patent No.: US 12,246,084 B2
(45) Date of Patent: *Mar. 11, 2025

(54) HAIR CARE COMPOSITION

(71) Applicant: Conopco, Inc., Englewood Cliffs, NJ (US)

(72) Inventors: Jingjing Liu, Shanghai (CN); Yingying Pi, Shanghai (CN); Xia Zheng, Shanghai (CN)

(73) Assignee: Conopco, Inc., Hoboken, NJ (US)

( * ) Notice: Subject to any disclaimer, the term of this patent is extended or adjusted under 35 U.S.C. 154(b) by 544 days.

This patent is subject to a terminal disclaimer.

(21) Appl. No.: 17/628,356

(22) PCT Filed: Jun. 29, 2020

(86) PCT No.: PCT/EP2020/068254
§ 371 (c)(1),
(2) Date: Jan. 19, 2022

(87) PCT Pub. No.: WO2021/013476
PCT Pub. Date: Jan. 28, 2021

(65) Prior Publication Data
US 2022/0265541 A1 Aug. 25, 2022

(30) Foreign Application Priority Data
Jul. 22, 2019 (WO) ............... PCT/CN2019/097153
Aug. 30, 2019 (EP) .................................... 19194658

(51) Int. Cl.
A61K 8/81 (2006.01)
A61K 8/46 (2006.01)
A61K 8/49 (2006.01)
A61K 8/891 (2006.01)
A61Q 5/00 (2006.01)
A61Q 5/12 (2006.01)

(52) U.S. Cl.
CPC ............ A61K 8/8158 (2013.01); A61K 8/463 (2013.01); A61K 8/4926 (2013.01); A61K 8/891 (2013.01); A61Q 5/006 (2013.01); A61Q 5/12 (2013.01); A61K 2800/5426 (2013.01)

(58) Field of Classification Search
CPC .... A61K 8/8158; A61K 8/463; A61K 8/4926; A61K 8/23; A61K 2800/5426; A61K 8/891; A61Q 5/006; A61Q 5/12
See application file for complete search history.

(56) References Cited

U.S. PATENT DOCUMENTS

| 3,958,581 A | 5/1976 | Abegg et al. |
| 3,962,418 A | 6/1976 | Birkofer |
| 5,194,639 A | 3/1993 | Connor et al. |
| 6,861,397 B2 | 3/2005 | Seitz, Jr. et al. |
| 9,662,291 B2 | 5/2017 | Johnson et al. |
| 10,463,597 B2 | 11/2019 | Jayaswal et al. |
| 10,881,597 B2 | 1/2021 | Lane et al. |
| 2002/0077256 A1 | 6/2002 | Niemiec et al. |
| 2003/0176303 A1 | 9/2003 | Niemiec et al. |
| 2008/0206355 A1 | 8/2008 | Schwartz et al. |
| 2009/0169644 A1 | 7/2009 | Goddinger et al. |
| 2013/0089586 A1* | 4/2013 | Johnson ............... A61K 8/0241 514/188 |
| 2014/0348886 A1 | 11/2014 | Johnson et al. |
| 2015/0157548 A1 | 6/2015 | De Feij et al. |
| 2017/0252277 A1 | 9/2017 | Staudigel |
| 2018/0015009 A1 | 1/2018 | Soubiran et al. |
| 2019/0000735 A1 | 1/2019 | Kelly et al. |

FOREIGN PATENT DOCUMENTS

| CN | 101804014 | 8/2010 | |
| CN | 104207966 | 12/2014 | |
| CN | 109010128 | 12/2018 | |
| CN | 109952088 | 6/2019 | |
| EP | 0455185 | 11/1991 | |
| RU | 2272612 | 3/2006 | |
| RU | 2688667 | 5/2019 | |
| TW | 201317007 | 5/2013 | |
| WO | WO9206154 | 4/1992 | |
| WO | WO9631188 | 10/1996 | |
| WO | WO9852518 | 11/1998 | |
| WO | WO2011003068 | 1/2011 | |
| WO | WO2013011122 | 1/2013 | |
| WO | WO2013050241 | 4/2013 | |
| WO | WO-2013050241 A1 * | 4/2013 | ........... A61K 8/4946 |
| WO | WO2014190132 | 11/2014 | |
| WO | WO2015054026 | 4/2015 | |
| WO | WO2016054450 | 4/2016 | |
| WO | WO2016054451 | 4/2016 | |
| WO | WO2017087028 | 5/2017 | |

(Continued)

OTHER PUBLICATIONS

Nutrition Shampoo, Mintel GNPD, Mar. 27, 2019 (Year: 2019).*
Search Report and Written Opinion in EP19194658; Mar. 25, 2020.
Shi Dan Li Cosmetics, Bei Rou Bio-Technology; Nutirition Shampoo,; Nutrition Shampoo, Five Cereal's Fragrant; May 24, 2019; Whole Document; Mintel—online.
Bo Ran Tang Bio-Tech; Alquemarine Strengthen & Repair Shampoo for Man; Hair Product; Mar. 27, 2019; Whole Document; Mintel—Online.
Search report and Written Opinion in PCTEP2020068254; Aug. 18, 2020.
Alquemarine Strengthen & Repair Shampoo for Man, Record ID 6435423; Mintel GNPD; May 24, 2019; pp. 1-4.

(Continued)

Primary Examiner — Blessing M Fubara
(74) Attorney, Agent, or Firm — Stephanie S. DelPonte

(57) ABSTRACT

A hair care composition is disclosed comprising an anti-dandruff agent selected from piroctone olamine, selenium sulfide and mixtures thereof and a copolymer comprising acrylamidopropyltrimonium chloride, wherein the weight ratio of the amount of the copolymer to the amount of the anti-dandruff agent is in the range of from 1:5 to 1:1.

18 Claims, No Drawings

(56) References Cited

FOREIGN PATENT DOCUMENTS

| WO | WO2017152018 | 9/2017 |
|---|---|---|
| WO | WO2018007332 | 1/2018 |
| WO | WO2018200644 | 11/2018 |
| WO | WO2019072515 | 4/2019 |
| WO | WO2019074989 | 4/2019 |
| WO | WO2019209369 | 10/2019 |
| WO | WO2021013476 | 1/2021 |
| ZA | 985781 | 10/2000 |

OTHER PUBLICATIONS

Nutrion Shampoo, Record ID 3583395; Mintel GNDP; Mar. 27, 2019; pp. 1-4.
Written Opinion in PCTEP2020068254; Jun. 25, 2021.
Written Opinion 2 in PCTEP2020068254; Jun. 25, 2021.
Mintel GNPD; Anti-Dandruff Shampoo; Darrow Klinse; Oct. 2015; Record ID 3518939, pp. 1-2; Brazil.
Mintel GNPD; Anti-Dandruff Shampoo; Aroma do Campo Arovitan Clinical Eucalipto e Climbazol; Jan. 2012; Record ID 1693358, pp. 1-2; Brazil.
Mintel GNPD; Shampoo for Men; eGo Black; Dec. 2012; Record ID 1944789, pp. 1-2; Venezuela.
IPRP2 in PCTEP20200682854.; Sep. 28, 2021.
Search Report in EP20182357.2; Nov. 18, 2020.
Anonymous ; "Ashland brings enduring dimension to hair repair with the introduction of N-DurHance A-1000 conditioning polymer"; Ashland; https://investor.ashland.com/releasedetail.cfm?releaseid=836; 5 pages; XP002757185; 2014.
Search Report in EP21155345.8; Aug. 4, 2021.
"Anti-Dandruff Amino Acid", Mintel, Record ID 6980463; 2019.
Search Report and Written Opinion in PCT/EP2021/067029; Aug. 25, 2021.
IPRP in PCT/EP2021/067029; Sep. 12, 2022.
Search Report and Written Opinion in PCT/EP2021/086928; Mar. 29, 2022.
Sutyagin et al.; Chemistry and Physics of Polymers Manual; Ministry of Education of the Russian Federation Tomsk Polytechnic University; Editorial House of TPU Tomsk; 210 pages; 2003.

* cited by examiner

HAIR CARE COMPOSITION

CROSS-REFERENCE TO RELATED PATENT APPLICATIONS

This application is a U.S. National Phase Application under 35 U.S.C. § 371 of International Application No. PCT/EP2020/068254, filed Jun. 29, 2020, which claims the benefit of priority to PCT/CN2019/097153, filed on Jul. 22, 2019, and EP19194658.1, filed on Aug. 30, 2019, all of which are incorporated herein by reference in their entireties.

TECHNICAL FIELD OF THE INVENTION

This invention relates to hair care compositions, more particularly to hair care compositions comprising anti-dandruff agents and a copolymer comprising acrylamidopropyltrimonium chloride.

BACKGROUND OF THE INVENTION

Hair care compositions generally provide cleansing or conditioning benefits or a combination of the two. Such compositions typically comprise one or more cleansing surfactants which generally aid in cleaning the hair and the scalp free of undesirable soil, particles and fatty matter.

Dandruff control is an important aspect of hair cleansing and care. Anti-dandruff benefit has been provided through hair care compositions including shampoos and hair conditioners. Dandruff is an issue that affects many people globally. The condition is manifested by the shedding of clumps of dead skin cells from the scalp. These are white in colour and provide an aesthetically displeasing appearance. A factor that contributes to dandruff is certain members of the Malassezia yeasts. To combat these, anti-dandruff products have included certain anti-dandruff agents which have anti-fungal activity, for example, piroctone olamine (Octopirox®), selenium sulfide or combinations thereof. These anti-dandruff agents remove (or at least reduce the level of) the Malassezia from the scalp and provide moderately effective treatment of the dandruff condition. Such a product performs as a hair cleansing shampoo or as a hair conditioner while mitigating the causes of dandruff.

However, many anti-dandruff products do not provide sufficient anti-dandruff agent deposition onto scalp. Those anti-dandruff agents do not strongly adhere to scalp surfaces and are easily rinsed away during hair wash or shower, therefore provide little or no anti-dandruff efficacy. Consequently, needs exist for a hair care composition which provides improved deposition of anti-dandruff agents to maximize the effectiveness of such anti-dandruff agents.

Cationic polymers are often used to enhance the deposition of conditioning agents and/or anti-dandruff agents onto the hair and/or scalp. These polymers may be synthetic or natural polymers that have been modified with cationic substituents. The present inventors have now found unexpectedly that copolymers comprising acrylamidopropyltrimonium chloride, compared to traditional cationic deposition polymers such as cationic guar polymers, can enhance deposition of anti-dandruff agents.

Tests and Definitions

Hair Care Composition

"Hair care composition", as used herein, is meant to include a composition for topical application to hair and/or scalp of mammals, especially humans. Such a composition may be generally classified as leave-on or rinse off, and includes any product applied to a human body for also improving appearance, cleansing, odor control or general aesthetics. The composition of the present invention can be in the form of a liquid, lotion, cream, foam, scrub, gel, or bar. Non-limiting examples of such compositions include leave-on hair lotions, creams, and rinse-off shampoos, conditioners, shower gels, or toilet bar. The composition of the present invention is preferably a rinse-off composition, especially preferred being a shampoo or a conditioner and most preferably a shampoo.

Cationic Charge Density

"Cationic charge density", as used herein, refers to the number of cationic charges per weight unit of a given polymer. Cationic charge density can be calculated from the degree of substitution as described in WO 2013/011122, the disclosure of which is hereby incorporated by reference in its entirety but especially page 8 lines 8-17. For example, for cationic guar polymer obtained by reacting with 2,3-epoxypropyltrimethylammonium chloride, the cationic charge density may be calculated from the degree of substitution using the following equation:

$$\text{Cationic charge density in milliequivalents per gram (meq/g)} = \frac{DS \times 1000}{162 + 151 \times DS}$$

Water-Insoluble

"Water-insoluble", as used herein, refers to the solubility of a material in water at 25° C. and atmospheric pressure being 0.1% by weight or less.

Molecular Weight

"Molecular weight", as used herein, refers to the weight average molecular mass of a given polymer. The weight average molecular weight (WAVG MW) of a given polymer is determined by SEC (Size Exclusion Chromatography) analysis using absolute calibration (universal calibration). Polysaccharide standards pulluan and dextran were used for calibration.

Miscellaneous

Except in the examples, or where otherwise explicitly indicated, all numbers in this description indicating amounts of material or conditions of reaction, physical properties of materials and/or use may optionally be understood as modified by the word "about".

All amounts are by weight of the final hair care composition, unless otherwise specified. It should be noted that in specifying any ranges of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) mutatis mutandis.

SUMMARY OF THE INVENTION

In a first aspect, the present invention is directed to a hair care composition comprising:
(a) an anti-dandruff agent selected from piroctone olamine, selenium sulfide and mixtures thereof; and
(b) a copolymer comprising acrylamidopropyltrimonium chloride;
wherein the weight ratio of the amount of the copolymer to the amount of the anti-dandruff agent is in the range of from 1:5 to 1:1.

In a second aspect, the present invention is directed to a method of depositing anti-dandruff agents onto scalp comprising the step of applying the hair care composition of any embodiment of the first aspect of this invention onto scalp surfaces of an individual. The method is preferably for non-therapeutic benefits.

In a third aspect, the present invention is directed to use of acrylamidopropyltrimonium chloride/acrylamide copolymer for enhancing deposition of anti-dandruff agents onto scalp.

All other aspects of the present invention will more readily become apparent upon considering the detailed description and examples which follow.

DETAILED DESCRIPTION

The copolymer suitable for use in compositions of the present invention comprises acrylamidopropyltrimonium chloride. Preferably, the copolymer also comprises acrylamide in addition to the acrylamidopropyltrimonium chloride. Particularly preferred copolymer is a copolymer of acrylamidopropyltrimonium chloride and acrylamide.

The copolymer according to the present invention preferably has a charge density of from 1.0 to 3.0 meq per gram (meq/g), more preferably from 1.1 to 2.5 meq/g, more preferably still from 1.2 to 2.5 meq/g and most preferably from 1.3 to 2.5 meq/g. The copolymer preferably has a molecular weight of from 100,000 to 3,000,000 gram per mole (g/mol), more preferably from 500,000 to 2,800,000 g/mol, more preferably still from 800,000 to 2,500,000 g/mol, most preferably from 1,000,000 to 2,500,000 g/mol. An example of a suitable copolymer is commercially available from Ashland under the trade name N-Hance SP-100®. N-Hance SP-100® has a charge density of from 1.8 to 2.2 meq/g and a molecular weight of from 1,800,000 to 2,200,000 g/mol.

The hair care composition of the present invention typically comprises the copolymer in an amount of from 0.001 to 2%, more preferably from 0.01 to 1%, even more preferably from 0.01 to 0.8% and most preferably from 0.05 to 0.5%, based on total weight of the hair care composition and including all ranges subsumed therein.

The hair care composition comprises anti-dandruff agents, which are compounds that are active against dandruff and are typically anti-microbial agents and preferably anti-fungal agents. Suitable anti-dandruff agents that may be used in this invention are selected from piroctone olamine (Octopirox®), selenium sulfide and mixtures thereof. In an especially preferred embodiment, the anti-dandruff agent is piroctone olamine.

Typically, the hair care composition of the invention comprises the anti-dandruff agent in an amount of from 0.01 to 10%, more preferably from 0.01 to 5%, more preferably still from 0.05 to 2%, and most preferably from 0.05 to 1.5%, based on total weight of the hair care composition and including all ranges subsumed therein.

It has been found that the copolymer of the present invention unexpectedly enhances deposition of anti-dandruff agents. The composition comprises the copolymer and the anti-dandruff agent in a weight ratio of from 1:5 to 1:1, preferably from 1:4 to 1:1, and most preferably from 1:4 to 1:1.5.

The pH of the composition is preferably equal to or higher than 4.0, more preferably in the range of 4.0 to 7.0.

In addition to the copolymer, it is preferable that the hair care composition also comprises other cationic polymers. Suitable cationic polymers may be homopolymers or be formed from two or more types of monomers. The molecular weight of the polymer will generally be between 5,000 and 10,000,000 g/mol, typically at least 10,000 g/mol and preferably from 100,000 to 2,000,000 g/mol. The polymers will have cationic nitrogen containing groups such as quaternary ammonium or protonated amino groups, or a mixture thereof. The cationic nitrogen containing group will generally be present as a substituent on a fraction of the total monomer units of the cationic polymer. Thus when the polymer is not a homopolymer it can contain spacer non-cationic monomer units. The ratio of the cationic to non-cationic monomer units is selected to give a polymer having a cationic charge density in the required range.

Suitable cationic polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have $C_1$-$C_7$ alkyl groups, more preferably $C_1$-$C_3$ alkyl groups. Other suitable spacers include vinyl esters, vinyl alcohol, maleic anhydride, propylene glycol and ethylene glycol.

Preferably, the cationic polymer is a cationic polysaccharide polymer such as cationic guar, cationic starch, and cationic cellulose. Suitably, such cationic polysaccharide polymers have a molecular weight of from 100,000 g/mol to 2,300,000 g/mol, more preferably from 150,000 g/mol to 2,000,000 g/mol. Such cationic polysaccharide polymers preferably have a cationic charge density from 0.1 to 4 meq/g.

Cationic polysaccharide polymers suitable for use in compositions of this invention include those represented by the general formula:

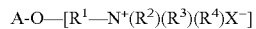

wherein: A is an anhydroglucose residual group, such as a starch or cellulose anhydroglucose residual. $R^1$ is an alkylene, oxyalkylene, polyoxyalkylene, or hydroxyalkylene group, or combination thereof. $R^2$, $R^3$ and $R^4$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^2$, $R^3$ and $R^4$) is preferably about 20 or less, and X is an anionic counterion.

Cationic cellulose is available from Amerchol Corp. (Edison, NJ, USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, NJ, USA) under the tradename Polymer LM-200.

Other suitable cationic polysaccharide polymers include quaternary nitrogen-containing cellulose ethers (e.g. as described in U.S. Pat. No. 3,962,418) and copolymers of etherified cellulose and starch (e.g. as described in U.S. Pat. No. 3,958,581).

A particularly preferred type of cationic polysaccharide polymer that can be used in compositions of the present invention is a cationic guar gum derivative, such as guar hydroxypropyltrimonium chloride (for example, commercially available from Solvay in their Jaguar trademark series or from Ashland in their N-Hance trademark series). Examples of such materials are Jaguar® C-13S, Jaguar® C-14S, Jaguar® C-17, Jaguar® Excel, Jaguar® C-162, Jaguar® C-500, Jaguar® Optima, Jaguar® LS, N-Hance™ BF17, N-Hance™ BF13 and N-Hance™ CCG45.

Mixtures of any of the above cationic polymers may be used. The cationic polymer preferably comprises cationic cellulose, cationic guar or mixtures thereof. Guar hydroxypropyltrimonium chloride is particularly preferred.

When used, the cationic polymer will generally be present in the hair care composition of the present invention in an amount of from 0.001 to 1% by weight of the hair care composition, more preferably from 0.01 to 0.5%, and most preferably from 0.03 to 0.3%, based on total weight of the hair care composition and including all ranges subsumed therein.

The hair care composition may additionally comprise a conditioning agent to provide conditioning benefit. Preferably, the hair care composition comprises discrete dispersed droplets of a water-insoluble conditioning agent, which has a mean droplet diameter ($D_{3,2}$) of less than 15 microns, preferably less than 10 microns, more preferably less than 5 microns, most preferably less than 3 microns. The mean droplet diameter ($D_{3,2}$) of a water-insoluble conditioning agent may be measured by means of a laser light scattering technique, for example using a 2600D Particle Sizer from Malvern Instruments.

The water-insoluble conditioning agent may include non-silicone conditioning agent comprising non-silicone oily or fatty materials such as hydrocarbon oils, fatty esters and mixtures thereof. Preferably, the water-insoluble conditioning agent is emulsified silicone oil.

Suitable silicones include polydiorganosiloxanes, in particular polydimethylsiloxanes which have the CTFA designation dimethicone. Also suitable for use in compositions of this invention (particularly shampoos and conditioners) are polydimethyl siloxanes having hydroxyl end groups, which have the CTFA designation dimethiconol. Also suitable for use in compositions of this invention are silicone gums having a slight degree of cross-linking, as are described for example in WO 96/31188. Preferably, the silicone oil comprises dimethicone, dimethiconol or a mixture thereof.

Suitable emulsified silicones for use in the hair care compositions of this invention are available as pre-formed silicone emulsions from suppliers of silicones such as Dow Corning and GE silicones. The use of such pre-formed silicone emulsion is preferred for ease of processing and control of silicone particle size. Such pre-formed silicone emulsions will typically additionally comprise a suitable emulsifier, and may be prepared by a chemical emulsification process such as emulsion polymerisation, or by mechanical emulsification using a high shear mixer. Examples of suitable pre-formed silicone emulsions include DC1785, DC1788, DC7128, all available from Dow Corning. These are emulsions of dimethiconol/dimethicone.

Another class of silicones which may be used are functionalized silicones such as amino functional silicones, meaning a silicone containing at least one primary, secondary or tertiary amine group, or a quaternary ammonium group. Examples of suitable amino functional silicones include polysiloxanes having the CTFA designation "amodimethicone."

The water-insoluble conditioning agent is generally present in hair care composition of this invention in an amount from 0.05 to 15%, preferably from 0.1 to 10%, more preferably from 0.5 to 8%, most preferably from 1 to 5%, based on total weight of the hair care composition and including all ranges subsumed therein.

In a preferred embodiment, the hair care composition is a shampoo. Thus in a preferred embodiment the composition comprises a cleansing surfactant. Non-limiting examples of suitable anionic cleansing surfactants are alkyl sulphates, alkyl ether sulphates, alkaryl sulphonates, alkanoyl isethionates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium and mono-, di- and triethanolamine salts. The alkyl and acyl groups generally contain from 8 to 18, preferably from 10 to 16 carbon atoms and may be unsaturated. The alkyl ether sulphates, alkyl ether sulphosuccinates, alkyl ether phosphates and alkyl ether carboxylic acids and salts thereof may contain from 1 to 20 ethylene oxide or propylene oxide units per molecule. Typical anionic cleansing surfactants for use in compositions of the invention include, but not limited to, sodium oeyl succinate, ammonium lauryl sulphosuccinate, sodium lauryl sulphate, sodium lauryl ether sulphate, sodium lauryl ether sulphosuccinate, ammonium lauryl sulphate, sodium dodecylbenzene sulphonate, triethanolamine dodecylbenzene sulphonate, sodium cocoyl isethionate, sodium lauryl isethionate, lauryl ether carboxylic acid, sodium N-lauryl sarcosinate or mixtures thereof. Preferred anionic cleansing surfactants are the alkyl sulphates and alkyl ether sulphates. Preferred alkyl sulphates are $C_{8-18}$ alky sulphates, more preferably $C_{12-18}$ alkyl sulphates, preferably in the form of a salt with a solubilising cation such as sodium, potassium, ammonium or substituted ammonium. Examples are sodium lauryl sulphate (SLS) or sodium dodecyl sulphate (SDS). It is particularly preferred that the anionic cleansing surfactant is alkyl ether sulphate. Preferred alkyl ether sulphates are those having the formula: $RO(CH_2CH_2O)_nSO_3M$; wherein R is an alkyl or alkenyl having from 8 to 18 (preferably 12 to 18) carbon atoms; n is a number having an average value of greater than at least 0.5, preferably between 1 and 3, more preferably between 2 and 3; and M is a solubilising cation such as sodium, potassium, ammonium or substituted ammonium. An example is sodium lauryl ether sulphate (SLES). Preferred alkyl ether sulphate is sodium lauryl ether sulphate having an average degree of ethoxylation of from 0.5 to 3, preferably from 1 to 3, more preferably from 2 to 3.

The anionic cleansing surfactants are typically present in hair care composition of the present invention at a level of from 0.5 to 45%, more preferably from 1.5 to 35% and most preferably from 5 to 20%, based on total weight of the hair care composition and including all ranges subsumed therein.

The composition as per the invention optionally and preferably additionally comprises co-surfactants such as amphoteric and zwitterionic surfactants to provide mildness to the composition. Suitable examples include alkyl amine oxides, alkyl betaines, alkyl amidopropyl betaines, alkyl sulphobetaines (sultaines), alkyl amphoacetates, alkyl amphopropionates, alkyl amidopropyl hydroxysultaines, wherein the alkyl group has from 8 to 19 carbon atoms. Preferably, the co-surfactant is a betaine surfactant. Cocamidopropyl betaine (CAPB) is particularly preferred.

When used, the co-surfactant typically makes up from 0.1 to 15%, more preferably from 0.5 to 8% and most preferably from 0.5 to 4% by weight of the hair care composition, based on total weight of the hair care composition and including all ranges subsumed therein.

Preferably the composition of the invention further comprises a suspending agent. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives, since these impart pearlescence to the composition. Polyacrylic acid is available commercially as Carbopol 420, Carbopol 488 or Carbopol 493. Polymers of acrylic acid cross-linked with a polyfunctional agent may also be used; they are available commercially as Carbopol 910, Carbopol 934, Carbopol 941 and Carbopol 980. An example of a suitable copolymer of a carboxylic acid containing monomer and acrylic acid esters is Carbopol 1342. All Carbopol (trademark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

Mixtures of any of the above suspending agents may be used. Preferred is a mixture of cross-linked polymer of acrylic acid and crystalline long chain acyl derivative.

The suspending agent is generally present in hair care composition of this invention in an amount of from 0.1 to 10%, more preferably from 0.2 to 6%, and most preferably from 0.3 to 4%, based on total weight of the hair care composition and including all ranges subsumed therein.

Preservatives may also be incorporated into the hair care composition of this invention to protect against the growth of potentially harmful microorganisms. Suitable traditional preservatives include alkyl esters of parahydroxybenzoic acid, hydantoin derivatives, propionate salts, and a variety of quaternary ammonium compounds. Illustrative yet non-limiting examples of the types of preservatives that may be used in this invention include, for examples, phenoxyethanol, sodium salicylate, methyl paraben, butyl paraben, propyl paraben, diazolidinyl urea, sodium dehydroacetate, benzyl alcohol, sodium benzoate, iodopropynyl butylcarbamate, caprylyl glycol, disodium EDTA or mixtures thereof. In an especially preferred embodiment, the preservative is sodium benzoate, phenoxyethanol, sodium salicylate or a mixture thereof. Preservatives are preferably employed in amounts ranging from 0.01 to 2% by weight of the hair care composition.

The hair care composition of the present invention may contain other ingredients which are common in the art to enhance physical properties and performances. Suitable ingredients include but are not limited to fragrance, dyes and pigments, pH adjusting agents, pearlescers or opacifiers, viscosity modifiers, thickeners, and natural hair nutrients such as botanicals, fruit extracts, sugar derivatives and amino acids.

The compositions of the invention are primarily intended for topical application to scalp and/or at least a portion of the hair of an individual, either in rinse-off or leave-on compositions, preferably in rinse-off compositions like shampoos.

The following examples are provided to facilitate an understanding of the present invention. The examples are not provided to limit the scope of the claims.

EXAMPLES

Example 1

This example demonstrated the weight ratio of copolymer to anti-dandruff agent can affect the deposition of anti-dandruff agent onto scalp. All ingredients are expressed by weight percent of the total formulation, and as level of active ingredient.

TABLE 1

| | Samples | | | |
|---|---|---|---|---|
| Ingredient | 1 | 2 | 3 | 4 |
| Water | Balance | Balance | Balance | Balance |
| Sodium lauryl ether sulphate | 12.65 | 12.65 | 12.65 | 12.65 |
| Piroctone olamine (Octopirox ®) | 0.75 | 0.75 | 0.75 | 0.75 |
| Disodium EDTA | 0.05 | 0.05 | 0.05 | 0.05 |
| Carbopol 980 | 0.35 | 0.35 | 0.35 | 0.35 |
| Acrylamidopropyltrimonium chloride/acrylamide copolymer[a] | 0.05 | 0.10 | 0.20 | 0.40 |
| Cocoamidopropyl betaine | 1.00 | 1.00 | 1.00 | 1.00 |
| Perfume | 0.75 | 0.75 | 0.75 | 0.75 |
| Dimethicone (DC7128)[b] | 0.52 | 0.52 | 0.52 | 0.52 |
| Dimethiconol (DC1788)[c] | 0.78 | 0.78 | 0.78 | 0.78 |
| Glycol Distearate | 0.645 | 0.645 | 0.645 | 0.645 |
| Sodium benzoate | 0.50 | 0.50 | 0.50 | 0.50 |
| Citrate acid | 0.55 | 0.55 | 0.55 | 0.55 |
| Sodium chloride | 0.80 | 0.80 | 0.80 | 0.80 | a. Commercial acrylamidopropyltrimonium chloride/acrylamide copolymer under the trade name N-Hance SP100 from Ashland.

b. Commercial dimethicone pre-blended with poloxamer from Dow Corning which has a particle size of 10 µm.

c. Commercial dimethiconol from Dow Corning which has a particle size of 0.2 µm.

Methods

About 0.2 grams of the test sample was taken on artificial skin (VITRO-SKIN from IMS testing group). This was diluted with 1.8 mL water and rubbed with a plastic rod for 30 seconds. The artificial skin surface was then rinsed twice with water, first time with 4 mL water for 30 second and then again with 4 mL water for 30 seconds. The deposition of piroctone olamine on the skin (10.75 $cm^2$ per plate) was measured using HPLC method.

Results

The average deposition (of five such experiments) are summarized in Table 2 (error represents standard deviation for duplicate measurements).

TABLE 2

| Samples | 1 | 2 | 3 | 4 |
|---|---|---|---|---|
| Piroctone olamine deposition (µg/plate) | 24.17 ± 5.74 | 22.08 ± 2.87 | 33.30 ± 3.96 | 36.89 ± 3.34 |

Samples 3 and 4 comprising a higher weight ratio of copolymer to piroctone olamine showed significantly better ($p < 0.05$) deposition of piroctone olamine compared to samples 1 and 2.

Example 2

This example is about using different anti-dandruff agents. Compositions were prepared according to the formulations detailed in Table 3. All ingredients are expressed by weight percent of the total formulation, and as level of active ingredient.

TABLE 3

| | Samples | | | |
|---|---|---|---|---|
| Ingredient | 5 | 6 | 7 | 8 |
| Water | Balance | Balance | Balance | Balance |
| Sodium lauryl ether sulphate | 12.65 | 12.65 | 12.65 | 12.65 |
| Climbazole | — | — | 0.75 | 0.75 |
| Piroctone olamine (Octopirox) | 0.75 | 0.75 | — | — |
| Propylene glycol | 1.00 | 1.00 | 1.00 | 1.00 |
| Carbopol 980 | 0.35 | 0.35 | 0.35 | 0.35 |
| Guar hyroxypropyltrimonium chloride[d] | 0.20 | — | 0.20 | — |
| Acrylamidopropyltrimonium chloride/acrylamide copolymer[a] | — | 0.20 | — | 0.20 |
| Cocoamidopropyl betaine | 1.00 | 1.00 | 1.00 | 1.00 |
| Perfume | 0.75 | 0.75 | 0.75 | 0.75 |
| Dimethicone (DC7128)[b] | 0.52 | 0.52 | 0.52 | 0.52 |
| Dimethiconol (DC1788)[c] | 0.78 | 0.78 | 0.78 | 0.78 |
| Glycol Distearate | 0.645 | 0.645 | 0.645 | 0.645 |
| Sodium benzoate | 0.50 | 0.50 | 0.50 | 0.50 |
| Citrate acid | 0.55 | 0.55 | 0.55 | 0.55 |
| Sodium chloride | 0.70 | 0.70 | 0.70 | 0.70 | d. Commercial guar hydroxypropyltnmonium chloride has a DS of 0.16 to 0.20 and a weight average molecular weight from 1.0 to 1.5 million g/mol under the trade name BB-18 from Lamberti.

Methods

About 0.2 grams of the test sample was taken on artificial skin (VITRO-SKIN from IMS testing group). This was diluted with 1.8 mL water and rubbed with a plastic rod for 30 seconds. The artificial skin surface was then rinsed twice with water, first time with 4 mL water for 30 second and then again with 4 mL water for 30 seconds. The deposition of piroctone olamine or climbazole on the skin (10.75 cm$^2$ per plate) was measured using HPLC method.

Results

The average deposition (of five such experiments) are summarized in Table 4 (error represents standard deviation for duplicate measurements).

TABLE 4

| Samples | 5 | 6 | 7 | 8 |
|---|---|---|---|---|
| Piroctone olamine deposition (µg/plate) | 10.16 ± 0.97 | 14.38 ± 2.8 | — | — |
| Climbazole deposition (µg/plate) | — | — | 8.11 ± 2.03 | 7.65 ± 1.00 |

It can be seen from the results that sample 6 comprising acrylamidopropyltrimonium chloride/acrylamide copolymer enhanced the deposition of piroctone olamine compared to sample 5 comprising cationic guar, while sample 8 showed comparable deposition of climbazole to sample 7.

The invention claimed is:

1. A hair care composition comprising:
   a) an anti-dandruff agent selected from piroctone olamine, selenium sulfide, and mixtures thereof; and
   b) a copolymer wherein the copolymer is acrylamidopropyltrimonium chloride/acrylamide copolymer;
   wherein the weight ratio of the amount of the copolymer to the amount of the anti-dandruff agent is in the range of from 1:5 to 1:1.

2. The hair care composition according to claim 1, wherein the composition comprises the anti-dandruff agent in an amount of from 0.01 to 10% by weight of the composition.

3. The hair care composition according to claim 2, wherein the composition comprises the anti-dandruff agent in an amount of from 0.01 to 5% by weight of the composition.

4. The hair care composition according to claim 1, wherein the weight ratio of the amount of the copolymer to the amount of the anti-dandruff agent is in the range of from 1:4 to 1:1.

5. The hair care composition according to claim 4, wherein the weight ratio of the amount of the copolymer to the amount of the anti-dandruff agent is in the range of from 1:4 to 1:1.5.

6. The hair care composition according to claim 1, wherein the composition comprises a cleansing surfactant.

7. The hair care composition according to claim 6, wherein the cleansing surfactant comprises sodium lauryl ether sulphate.

8. The hair composition according to claim 1, wherein the composition comprises a conditioning agent.

9. The hair composition according to claim 8, wherein the conditioning agent is a silicone oil.

10. The hair composition according to claim 9, wherein the conditioning agent is selected from dimethicone, dimethiconol, or a mixture thereof.

11. The hair care composition according to claim 1, wherein the composition additionally comprises a cationic polymer.

12. The hair care composition according to claim 11, wherein the cationic polymer is cationic cellulose, cationic guar, or mixtures thereof.

13. The hair care composition according to claim 12, wherein the cationic guar is guar hydroxypropyltrimonium chloride.

14. The hair care composition according to claim 1, wherein the composition is a shampoo.

15. A method of depositing anti-dandruff agents onto scalp comprising a step of applying the hair care composition according to claim 1 onto scalp surfaces of an individual followed by rinsing the surfaces with water.

16. The method according to claim 15, wherein the anti-dandruff agent is piroctone olamine.

17. A hair care composition comprising:
   a) from 0.01 to 0.75 wt % of an anti-dandruff agent wherein the anti-dandruff agent is piroctone olamine;
   b) from 0.2 to 1 wt % a copolymer wherein the copolymer is acrylamidopropyltrimonium chloride/acrylamide copolymer; and
   c) from 5 to 20 wt % of an anionic surfactant wherein the anionic surfactant is sodium lauryl ether sulphate wherein the weight ratio of the amount of the copolymer to the amount of the anti-dandruff agent is in the range of from 1:5 to 1:1.

18. A hair care composition comprising:
a) from 0.01 to 0.75 wt % of an anti-dandruff agent wherein the anti-dandruff agent is selenium sulfide;
b) from 0.2 to 1 wt % a copolymer wherein the copolymer is acrylamidopropyltrimonium chloride/acrylamide copolymer; and
c) from 5 to 20 wt % of an anionic surfactant wherein the anionic surfactant is sodium lauryl ether sulphate wherein the weight ratio of the amount of the copolymer to the amount of the anti-dandruff agent is in the range of from 1:5 to 1:1.

* * * * *